United States Patent [19]

Appelgren et al.

[11] Patent Number: 4,981,695
[45] Date of Patent: Jan. 1, 1991

[54] COMPOSITION COMPRISING L-DOPA

[75] Inventors: Curt H. Appelgren, Kungsbacka; Eva C. Eskilsson, Mölnlycke, both of Sweden

[73] Assignee: Lejus Medical Aktiebolag, Molndal, Sweden

[21] Appl. No.: 378,423

[22] Filed: Jul. 12, 1989

Related U.S. Application Data

[63] Continuation of Ser. No. 89,655, Aug. 26, 1987, abandoned.

[30] Foreign Application Priority Data

Aug. 26, 1986 [SE] Sweden .................. 8603582-1

[51] Int. Cl.$^5$ .................. A61K 9/54; A61K 9/16
[52] U.S. Cl. .................. 424/456; 424/463; 424/494; 514/252; 514/781; 514/962; 514/963; 514/964; 514/965
[58] Field of Search .................. 424/456, 463, 494; 514/962, 963, 964, 965, 252, 781

[56] References Cited

U.S. PATENT DOCUMENTS 3,957,523  5/1976  Ohno et al. .................. 424/362
4,021,555  5/1977  Seyfried et al. .................. 514/252
4,446,138  5/1984  Pack .................. 514/239

FOREIGN PATENT DOCUMENTS

0156077A1  10/1985  European Pat. Off. .
1128461    12/1971  Fed. Rep. of Germany .
1116256    12/1970  France .
2242076     8/1975  France .
59-139317   8/1984  Japan .................. 424/456
7512740-7  12/1975  Sweden .
2057876     4/1981  United Kingdom .................. 424/494

*Primary Examiner*—Mark L. Bell
*Assistant Examiner*—Anthony J. Green
*Attorney, Agent, or Firm*—Millen, White & Zelano

[57] ABSTRACT

The present invention relates to a multiple-unit-dose comprising L-dopa as pharmaceutically active compound, whereby the composition provides a release of L-dopa in accordance with a test in accordance with U.S. Pharmacopeia Standards in an artificial gastric juice having a pH of at most 1.2 of at most 20% by weight during 1 hr, and in a phosphate buffer according to the same standard a release of at least 35% by weight during 1 hr, and at least 80% by weight during 3 hrs.

7 Claims, 14 Drawing Sheets

Figure 15:
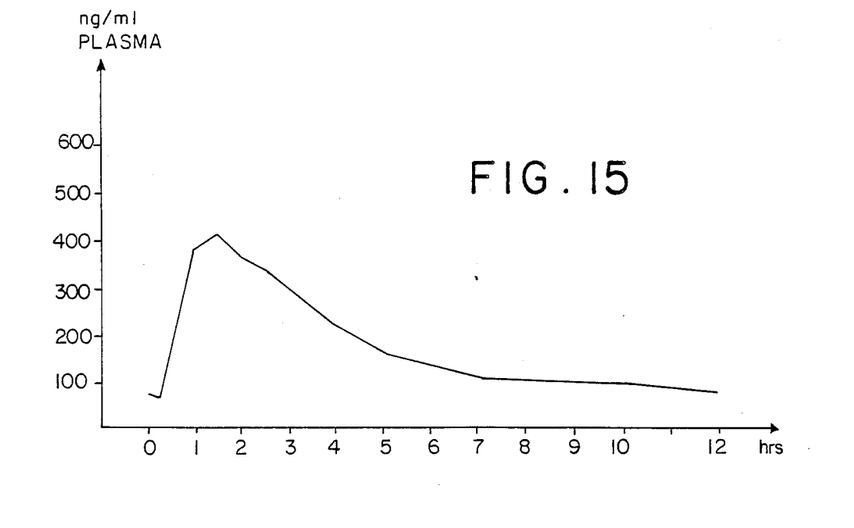
Figure 15A:
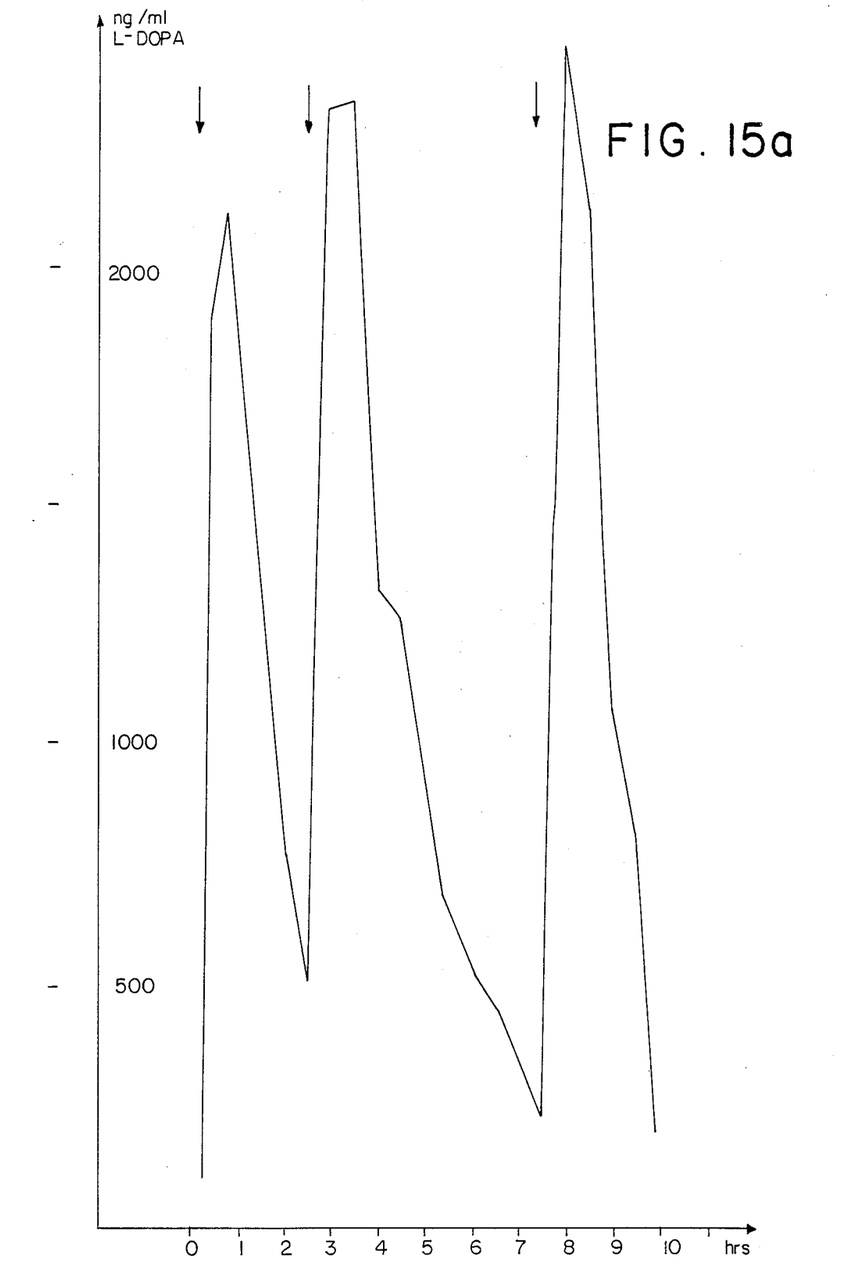
Figure 15B:
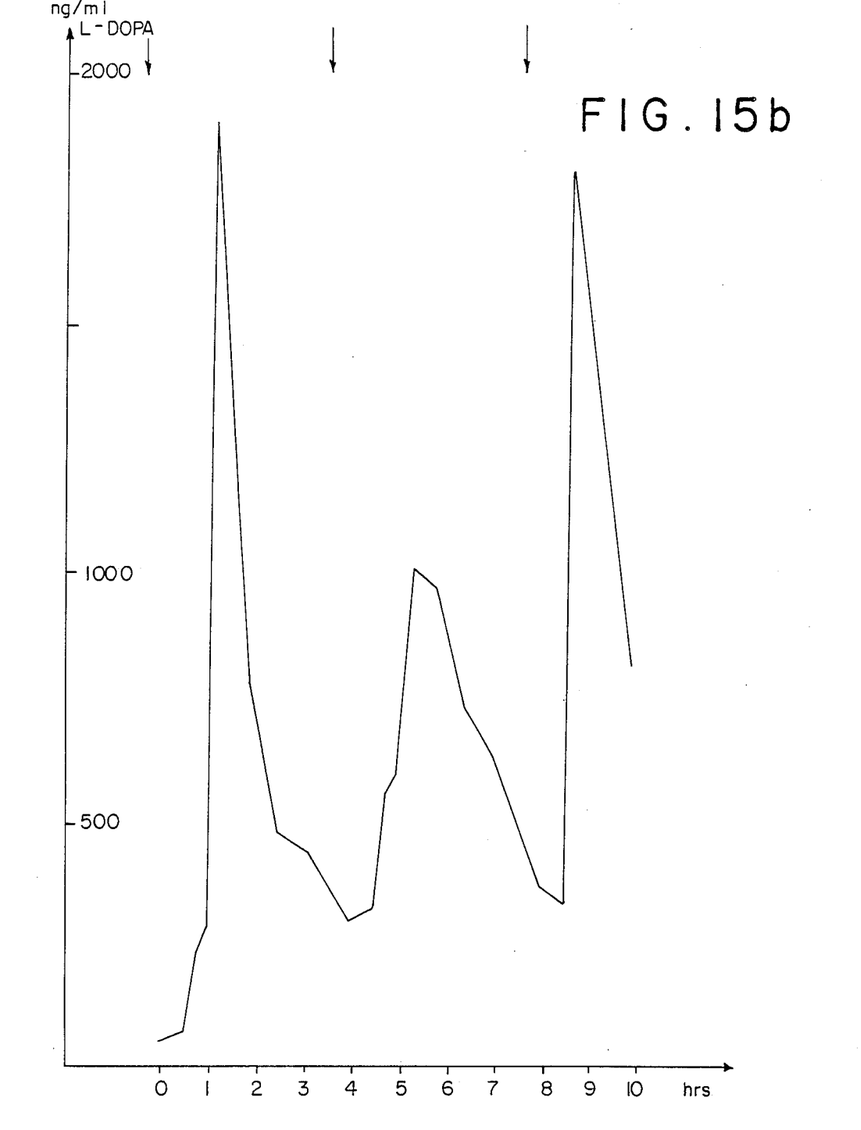

FIG. 15b ical composition, whereby cores comprising L-dopa are
COMPOSITION COMPRISING L-DOPA This application is a continuation of application Ser. No. 07/089,655, filed Aug. 26, 1987, abandon.

TECHNICAL FIELD

The present invention relates to a multiple-unit-dosage composition comprising as a pharmaceutically active compound L-dopa, i.e., L-3,4-dihydroxyphenylalanine.

The object of the present invention is to obtain a pharmaceutical composition comprising as a pharmaceutically active compound L-dopa, to obtain by means of this in the form of a multiple-unit-dosage a usable L-dopa composition, which gives a high bioavailability, i.e., gives good pharmacologically active plasma levels at an administration twice to four times a day.

BACKGROUND OF THE INVENTION

L-dopa, L-3,4-dihydroxyphenyl alanine, or 3-(3,4-dihydroxy-phenyl)-L-alanine, or 3-hydroxy-L-tyrosine, alternatively, is a pharmaceutically active compound, which is active at the inhibition of symptoms of the Parkinsons disease, particularly at the inhibition of the tremor related to the Parkinsons disease.

However, hitherto has no pharmaceutical composition been developed which gives a satisfactory pharmacological effect, i.e., a pharmaceutically high, even plasma level. This depends on several factors, i.a., that L-dopa is rapidly decomposed by carboxylic elimination. This can, and has been regulated by adding a decarboxylase inhibitor, such as benserazide or carbidopa, the administration of which means that the L-dopa dose can be considerably reduced. Other problems are that L-dopa is resorbed over a restricted part of the gastrointestinal tract, i.e., shows a so called absorption window. Hitherto it has been necessary to administer known compositions five to eight times per 24 hrs due to the short half life time of L-dopa. In spite of this the treatment has given high top levels in the plasma which in turn leads to troublesome side-effects.

DESCRIPTION OF THE PRESENT INVENTION

It has now surprisingly been shown possible to solve the abovementioned problem and to obtain a pharmaceutically acceptable composition, which in vivo gives a balanced plasma level, whereby the invention is characterized in that the composition in a test according to US Pharmacopea Standards (USP XXI, apparatus 2, 100 rpm) in an artificial gastric juice without enzymes and having a pH of up to 1.2 gives a release of L-dopa of at most 20 % by weight during 1 hr, and in accordance with the same standard in a phosphate buffer having a pH of 6.8 releases at least 35 % by weight within 1 hr, and at least 80 % by weight within 3 hrs.

By means of the present invention an even level of active compound has thus been able to be obtained at the administration twice to four times per 24 hrs, simultaneously as the side effects have been reduced.

The present invention further comprises a process for preparing the present multiple-unit-dose pharmaceutical composition, whereby cores comprising L-dopa are coated with at least an anionic polymer having a $pk_a$ of 5.0-5.5 to give the release rates given above.

The term anionic polymer having $pk_a$ of 5.0-5.5 includes hydroxypropyl methylcellulose phthalate, cellulose acetate phthalate, polyvinyl acetate phthalate, and different Eudragit$^R$ qualities, such as S100, whereby these qualities includes methylmethacrylate methylesters.

The present invention will now be described more in detail in the following with reference to a number of examples which all meet the characteristic above. A couple of comparative examples will be shown.

EXAMPLES 1, A–C.

An uncoated granulate was prepared from 300 g of L-dopa, 470 g of mannitol, 60 g of Avicel PH 101 (microcrystalline cellulose), 70 g of L-HPC (low-substituted hydroxypropyl cellulose), and 100 g of ascorbic acid. The granulate present in the form of small spheres having a diameter of 0.5–1.5 mm was then coated according to the following.

EXAMPLE 1.

100 g of uncoated granulate were coated with 9.3 g of hydroxypropyl methylcellulose phthalate (HP55, $pk_a$ 5.5) to a granulate ready for administration, which was packed in capsules containing the dose 100 mg L-dopa per capsule.

EXAMPLE A.

100 g of uncoated granulate of above were coated with a laminate consisting of a first inner layer consisting of ethyl cellulose, 3.9 g, and Pharmacoat 603 (hydroxypropyl methylcellulose), 2.0 g, and a second outer layer consisting of 9.1 g of hydroxypropyl methylcellulose phthalate (HP55) to a granulate ready for administration, which was packed in capsules (100 mg of L-dopa per capsule; about 700 pieces of small spheres per capsule).

EXAMPLE B.

100 g of uncoated granulate of above were coated for comparative reasons with a laminate consisting of a first inner layer of 4.3 g of ethyl cellulose and 2.2 g of Pharmacoat 603, and a second outer layer of 7.0 g of hydroxypropyl methylcellulose phthalate (HP55) to a granulate ready for administration which was packed in capsules (100 mg of L-dopa per capsule).

EXAMPLE C.

For comparative reasons 100 g of uncoated granulate of above were coated with 6.7 g of Pharmacoat 603 to a granulate ready for administration, which was packed in capsules (100 mg of L-dopa per capsule).

Figure 1:
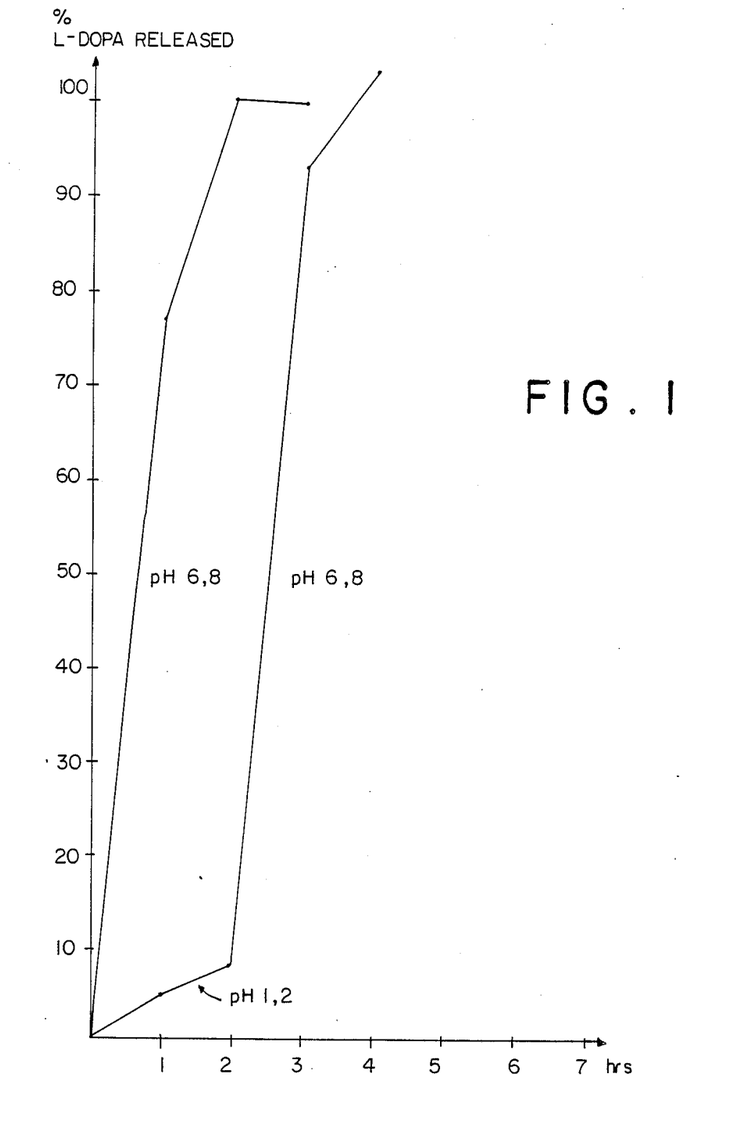
Figure 2:
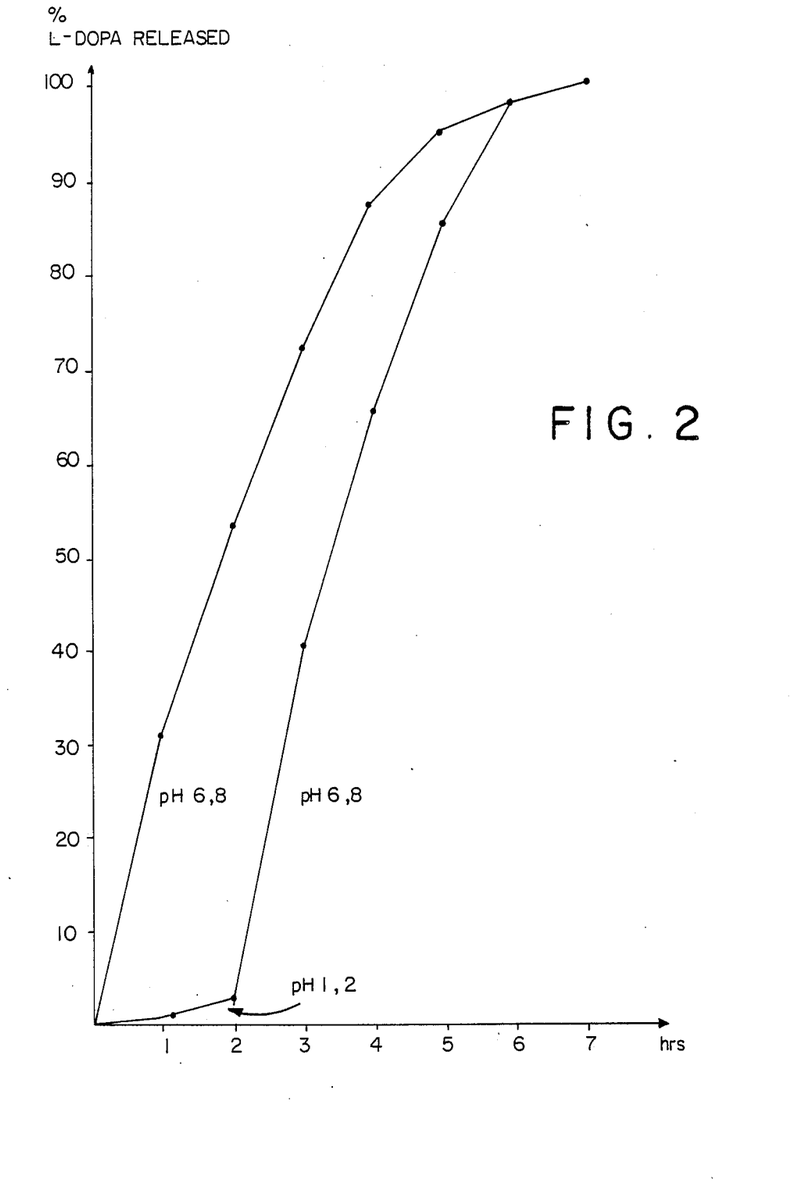
Figure 3:
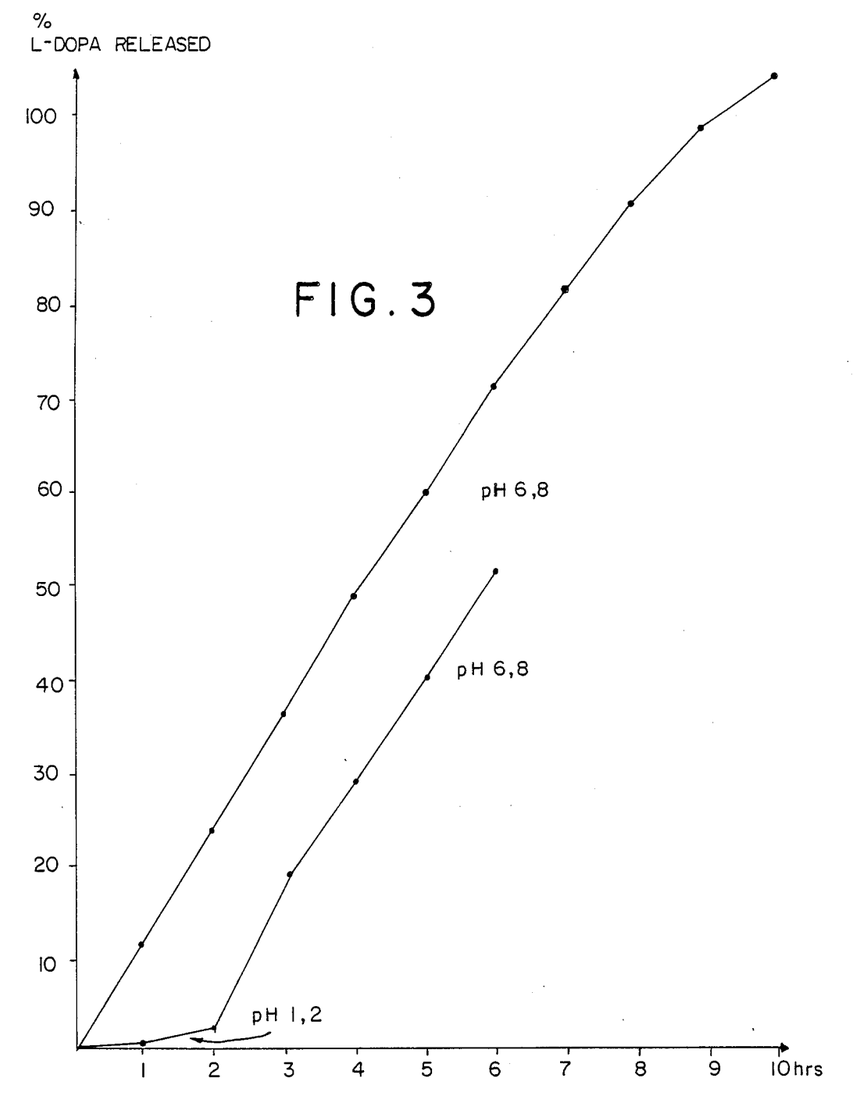
Figure 4:
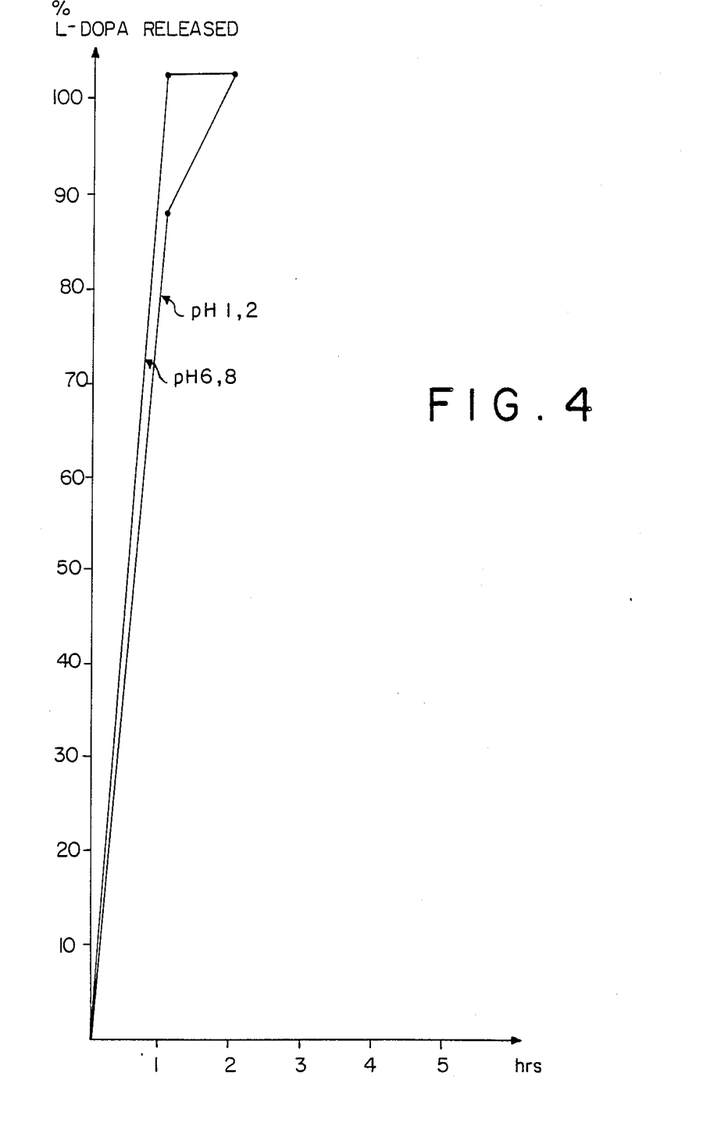
Figure 5:
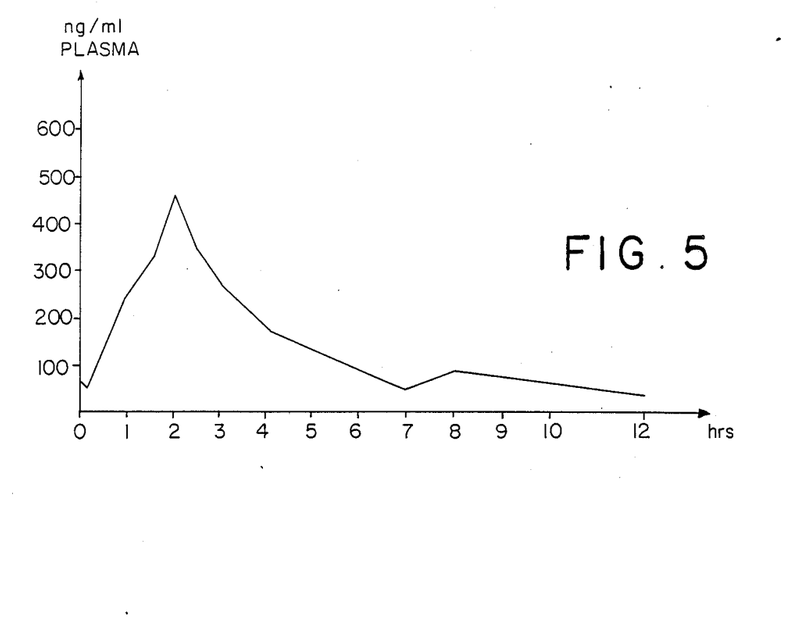
Figure 6:
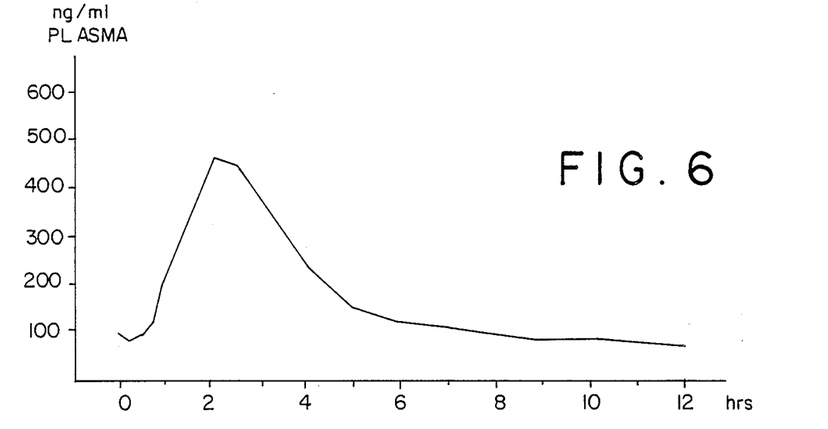

The compositions according to Ex. 1 and A–C above were tested by being run in an artificial gastric juice without enzymes, pH 1.2 in accordance with USP Standards (USP XXI, apparatus 2, 100 rpm) and then in a phosphate buffer pH 6.8 according to USP Standard (phosphate buffer: 0.2 M $KH_2PO_4$ 250 ml, 0.2 M NaOH 112 ml, deionized water to 1000 mls) for the study of the release rates, and in phosphate buffer pH 6.8 alone for the study of the release rates without preexposure in acidic environment. The results are shown in FIG. 1–4 (FIG. 1=Ex. 1; FIG. 2=Ex. A; FIG. 3=Ex. B; FIG. 4=Ex. C).

Figure 7:
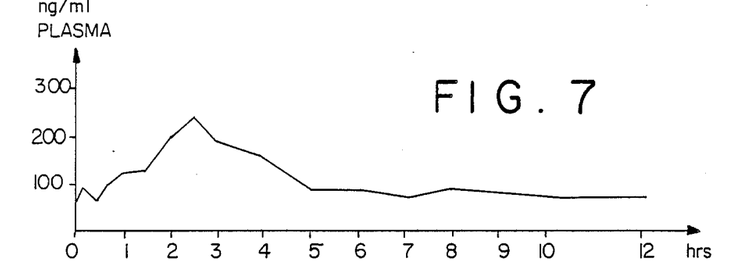
Figure 8:
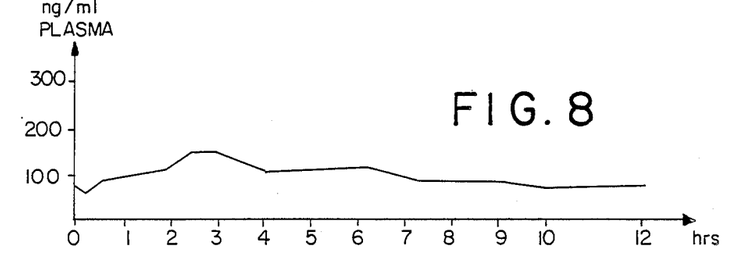
Figure 9:
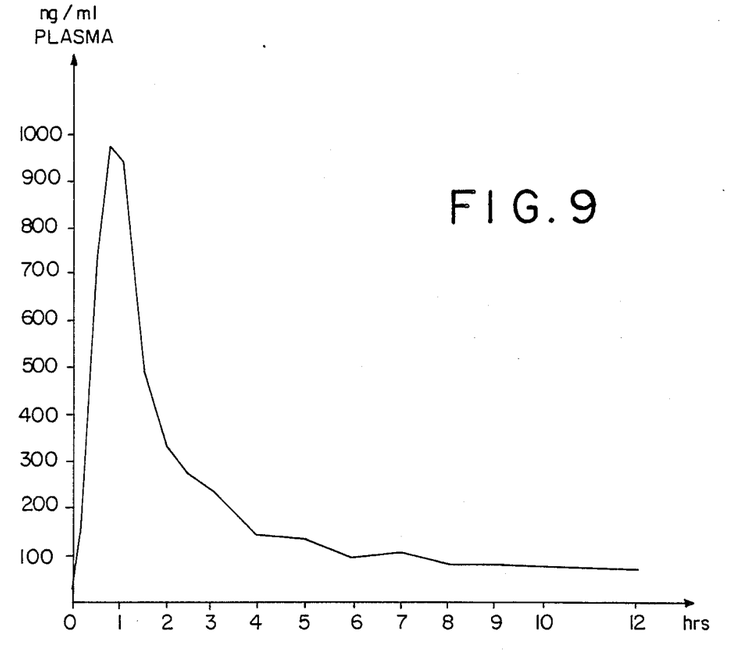

The compositions according to Ex. 1, and A–C where then tested in a single dose study on 10 healthy test persons each. The composition according to Ex. 1 took part in another study using single dose administration. The results are shown in FIG. 5–9 (FIG. 5,6=Ex.1; FIG. 7=Ex. A; FIG. 8=Ex. B; FIG. 9=Ex. C).

As evident from FIG. 3 a composition according to Ex. B has too a slow release in pH 6.8, and as evident from FIG. 4 a composition according to Ex. C has a total release in pH 1.2 within a short time.

The results evident from FIG. 2,3 and FIG. 4 are also confirmed by the results according to FIG. 7,8 and FIG. 9. As evident from FIG. 7 low plasma levels are obtained, and thereby too low a bioavailability; as evident from FIG. 8 no considerable plasma level at all; and as evident from FIG. 9 too a high initial concentration is obtained using a composition according to Ex. C, a concentration which decreases rapidly. As evident from FIG. 5 and 6 a composition according to Ex. 1 gives a considerably more even plasma level and thereby bioavailability. In accordance with FIG. 5 and 6 no strong plasma peaks are obtained.

EXAMPLE 2-5.

An uncoated granulate comprising a high dose of L-dopa was prepared as follows. 850 g of L-dopa were provided with 100 g of Avicel PH 101 (microcrystalline cellulose), 30 g of Tween 80 (polysorbitane ester), and 20 g of Ac-Di-Sol (cross linked Na-Carboxymethyl cellulose). The granulate in the form of small spheres, diameter 0.5–1.5 mm, was coated as follows.

EXAMPLE 2.

100 g of the uncoated granulate of above were coated in a fluidized bed with 12.0 g of hydroxypropyl methylcellulose phthalate (HP55) to a granulate ready to be administered, which was packed in gelatine capsules (100 mg of L-dopa per capsule).

EXAMPLE 3.

100 g of the uncoated granulate of above were coated using a mixture of 9.9 g of hydroxypropyl methylcellulose phthalate (HP55) and 2.1 g of ethyl cellulose to a granulate ready to be administered, which was packed in gelatine capsules (100 mg of L-dopa per capsule).

EXAMPLE 4.

100 g of the uncoated granulate of above were coated with a mixture of 7.2 g of Eudragit$^R$ S100 (methyl methacrylate methylesters comprising carboxylic acid groups) and 4.7 g of hydroxypropyl methylcellulose phthalate (HP55) to a granulate ready to be administered, which was packed in capsules (100 mg of L-dopa per capsule).

EXAMPLE 5.

100 g of uncoated granulate of above were coated with a laminate consisting of a first inner layer of 4.2 g of Pharmacoat 603, and 1.8 g of ethyl cellulose, and a second outer layer of 8.0 g of hydroxypropyl methylcellulose phthalate (HP50, $pk_a$ 5.0) to a granulate ready to be administered, which was packed in gelatine capsules (100 mg of L-dopa per capsule).

Figure 10:
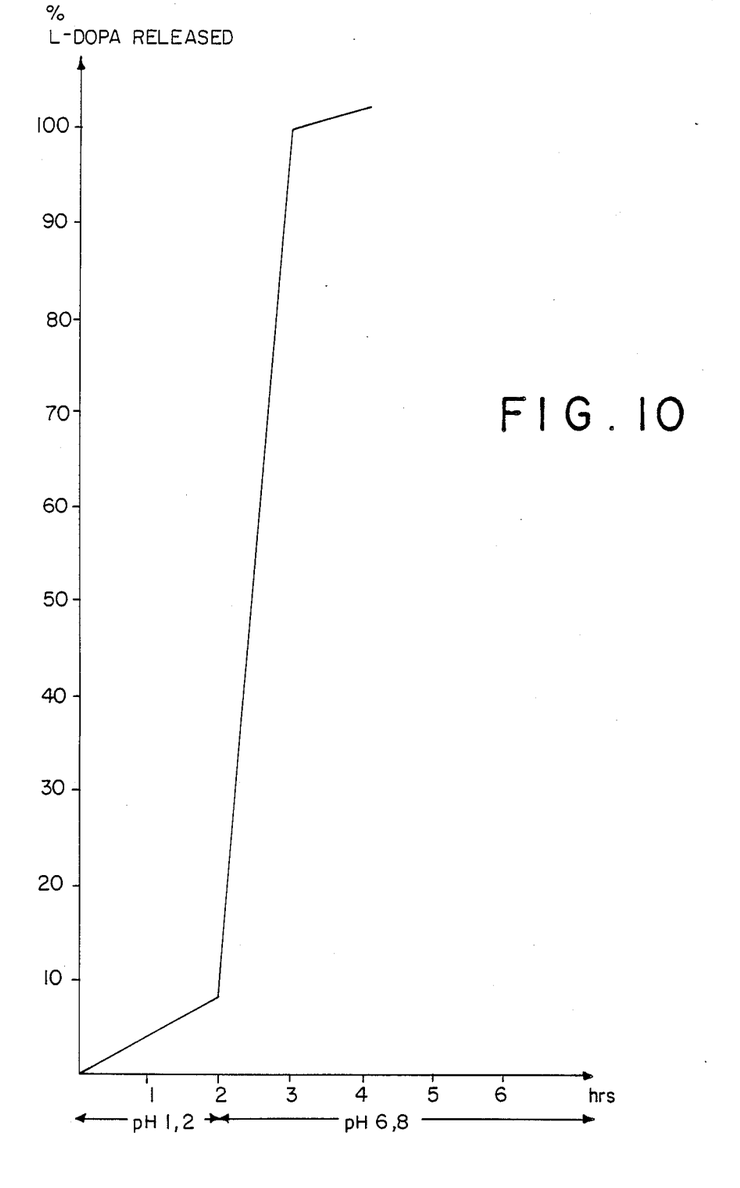
Figure 11:
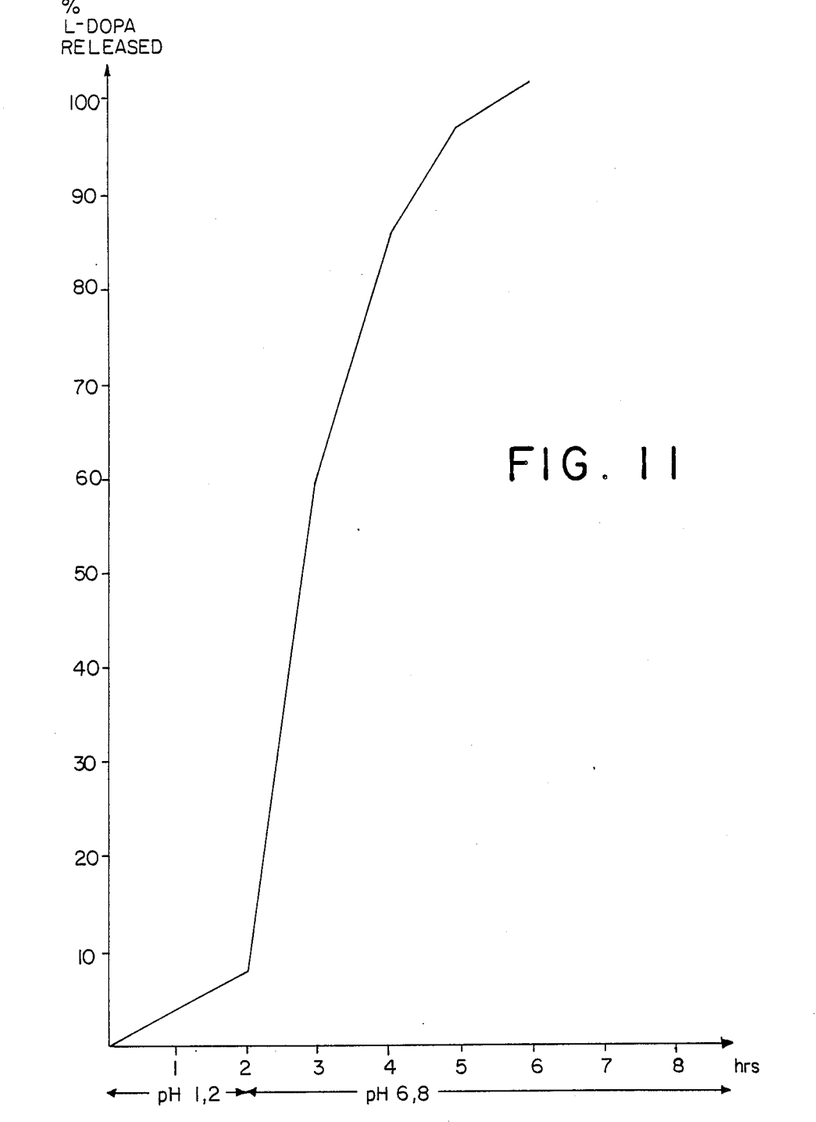
Figure 12:
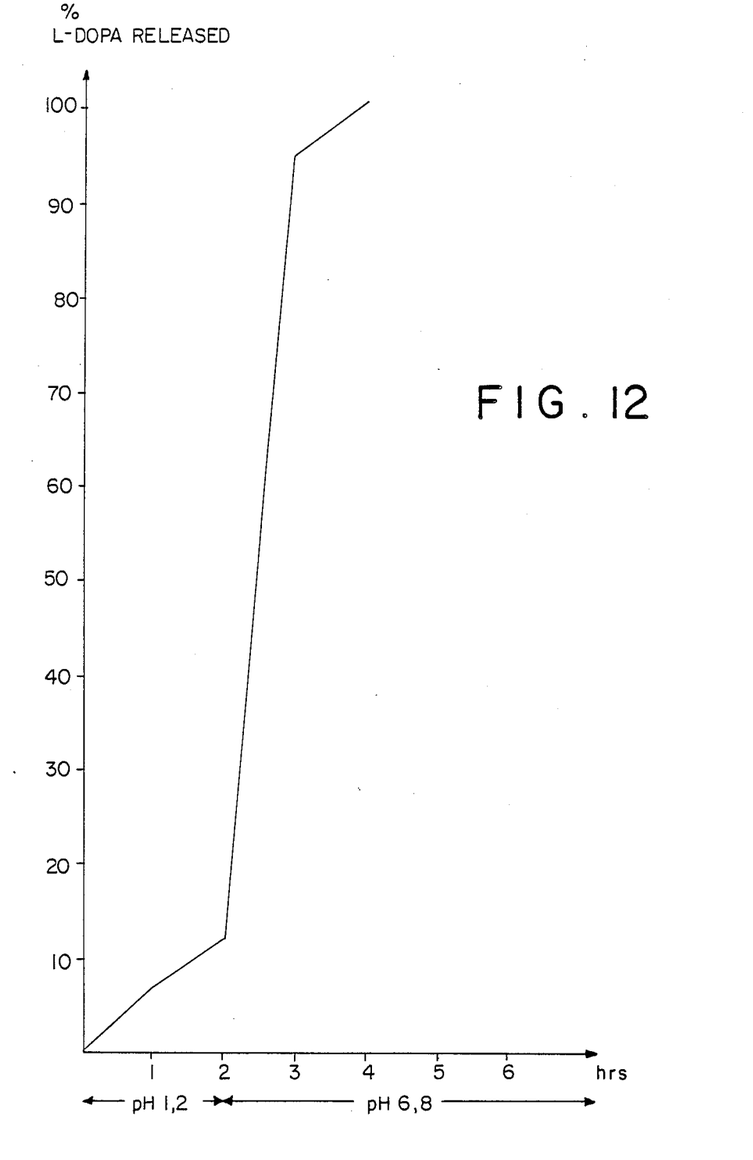
Figure 13:
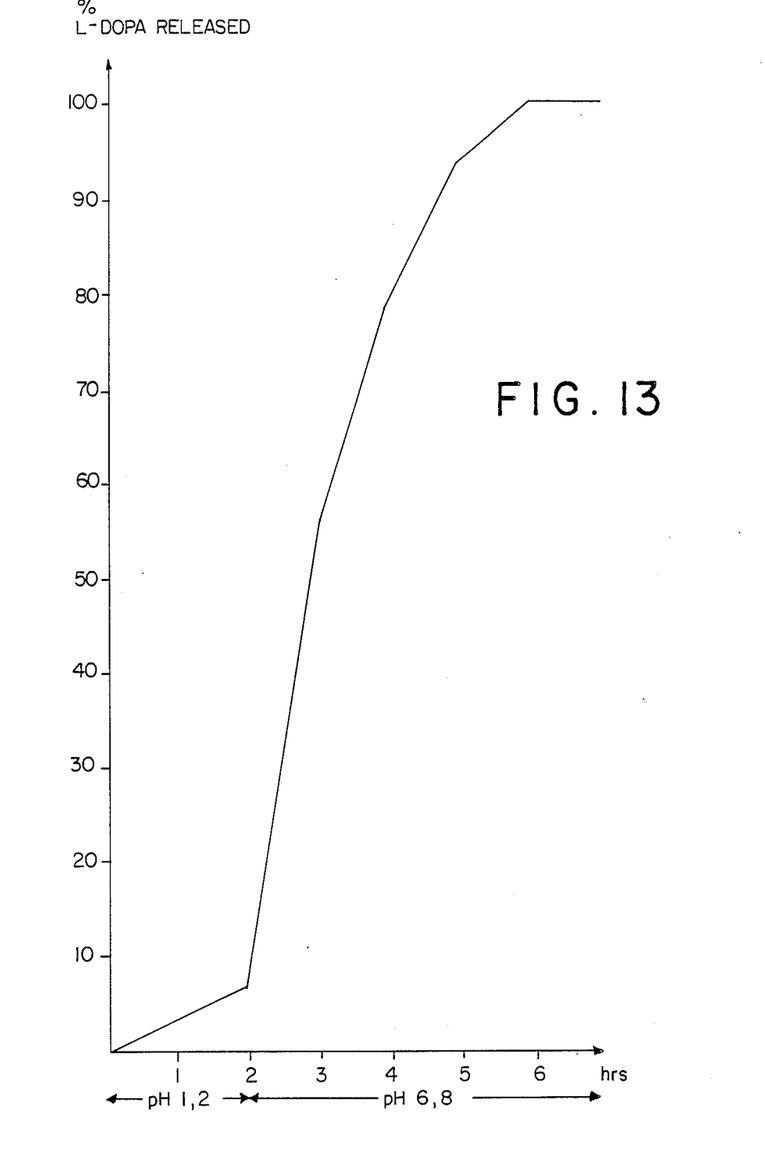

The compositions according to Examples 2-5 were tested with regard to the release rate of L-dopa in artificial gastric juice without enzymes in accordance with USP Standards (USP XXI, apparatus 2, 100 rpm), pH 1.2 for 2 hrs and then in a phosphate buffer pH 6.8. The results are given in FIG. 10-13 (FIG. 10=Ex. 2; FIG. 11=Ex. 3; FIG. 12=Ex. 4; FIG. 13=Ex. 5).

Figure 14:
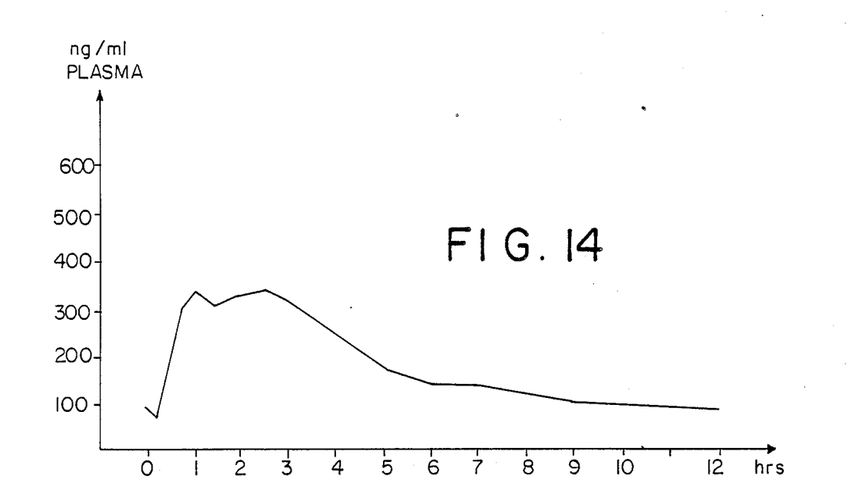

The compositions according to Examples 2 and 5 have also been tested in six healthy test persons each in a single dose study. The results are shown in FIG. 14-15. (FIG. 14=Ex. 2; FIG. 15=Ex. 5).

As evident from FIG. 10-13 the compositions according to Examples 2-5 meet the demands put forward, and as evident from FIG. 14 and 15 the compositions give even plasma levels, completely without interfering peak levels, which also gives good bioavailability.

Figure 14A:
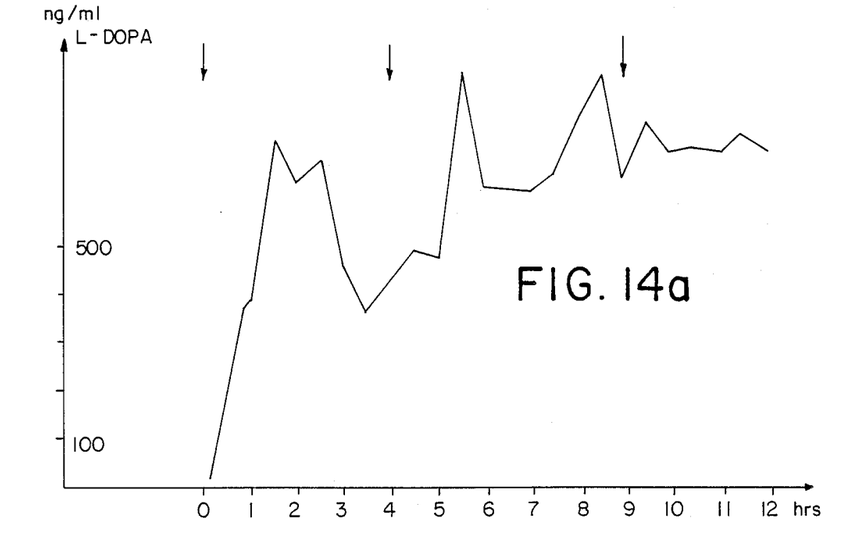
Figure 14B:
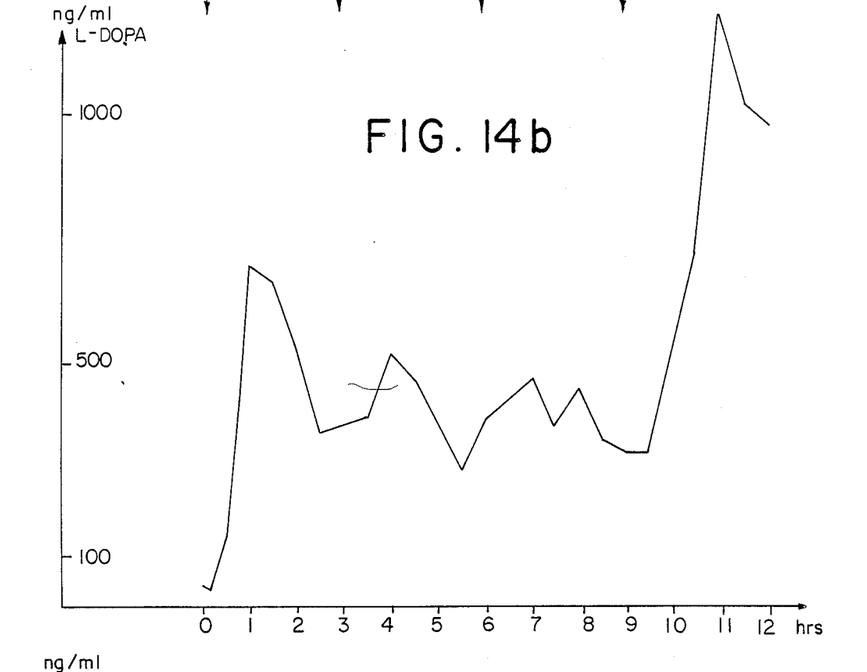

The composition according to the invention, Example 5 above, has also been tested in patients suffering from Parkinsons disease. The test was also compared with an L-dopa composition present on the market. FIG. 14a and 14b show the blood plasma levels using a composition of Example 5 in two patients, and FIG. 15a and 15b show the blood plasma levels using the composition of the market in the same two patients. The composition according to the invention was administered to patient 1, FIG. 14a, in doses containing 200 mg, 300 mg, and 300 mg per day, while the same patient obtained 250 mg of L-dopa three times a day using the marketed composition. Patient 2, FIG. 14b, and 15b, was given 100 mg of L-dopa of the composition of the invention four times a day, while the patient was given 125 mg of L-dopa of the marketed composition three times a day. Administration points are shown with arrows.

The term multiple-unit-dose above means a dose present in the form of a number of granules, or the like, which taken together give the dose size requested. Thus such a multiple-unit-dose can comprise from 100 to 1000 small granules having spherical or another shape.

Using a multiple-unit-dose, which is administered by means of a capsule, normally hard, or in a SACHET-bag, or using a measuring spoon or other measuring device, the small units will be distributed in the gastric juice and leak out little by little into the intestinal tract.

Using the present compositions, which are given orally, the pharmaceutically active dose of L-dopa divided into two to four doses per 24 hrs should be 100–1000 mg.

The compositions above can be completed with decarboxylase inhibitors of the above given type viz., benserazide and/or carbidopa or the compositions can be administered simultaneously with a decarboxylase inhibitor to obtain a better L-dopa effect.

I claim:

1. A solid particulate composition adapted for oral ingestion consisting essentially of particles having a core consisting essentially of 75–85% by weight of L-dopa coated with a laminate consisting of an inner layer of 3.2–4.5% by weight of hydroxypropyl methylcellulose, and 1.2–2.4% by weight of ethyl cellulose, and an outer layer of 6.0–0.9% by weight of hydroxypropyl methylcellulose phthalate having a $pk_a$ of 5.0, which composition in a release test according to US Pharmacopea Standards (USP XXI, apparatus 2, 100 rpm) in an artificial gastric juice without enzymes and having a pH of up to 1.2, releases at most 20% by weight of the L-dopa during one hour therein and thereafter in accordance with the same standard release method in a phosphate buffer having pH 6.8 releases at least 35% by weight of the L-dopa within the first hour therein and at least 80% by weight thereof within the next three hours therein.

2. A composition according to claim 1, wherein the core also contains at least one of benserazide and carbidopa in an amount effective to enhance the L-dopa effect.

3. A composition according to claim 1, wherein the release in artificial gastric juice is at most 10% by weight at pH 1.2 during 2 hours.

4. A composition according to claim 3, also containing at least one of benserazide and carbidopa in an amount effective to enhance the L-dopa effect.

5. A composition according to claim 3, in the form of granules.

6. A capsule or tablet containing the particulate composition according to claim 1.

7. A gelatin capsule containing granules according to claim 5.

* * * * *

UNITED STATES PATENT AND TRADEMARK OFFICE
CERTIFICATE OF CORRECTION

PATENT NO. : 4,981,695

DATED : January 1, 1991

INVENTOR(S) : Appelgren et al

It is certified that error appears in the above-identified patent and that said Letters Patent is hereby corrected as shown below:

Title Page, Assignee:

Reads: "Lejus Medical Aktiebolag, Molndal, Sweden"

Should Read: --ASTA PHARMA AKTIENGESELLSCHAFT, Frankfurt, Federal Republic of Germany--

Signed and Sealed this

Twenty-first Day of April, 1992

Attest:

HARRY F. MANBECK, JR.

*Attesting Officer*     *Commissioner of Patents and Trademarks*